(12) United States Patent
Kim et al.

(10) Patent No.: US 7,241,884 B2
(45) Date of Patent: Jul. 10, 2007

(54) PORPHINES-PLATINUM METAL COMPLEX COMPOUNDS FOR ORGANIC ELECTROLUMINESCENT DEVICE AND ORGANIC ELECTROLUMINESCENT DEVICE USING THEM

(75) Inventors: Sang-Dae Kim, Daegu (KR);
Yoon-Heung Tak, Kyongsangbuk-do (KR); Dong-Uk Kim, Daegu (KR);
Tae-Jeong Kim, Daegu (KR);
Ung-Chan Yoon, Busan (KR);
Sung-Hoon Kim, Daegu (KR);
Lee-Soon Park, Daegu (KR)

(73) Assignee: LG Electronics Inc., Seoul (KR)

( * ) Notice: Subject to any disclaimer, the term of this patent is extended or adjusted under 35 U.S.C. 154(b) by 24 days.

(21) Appl. No.: 10/959,107

(22) Filed: Oct. 7, 2004

(65) Prior Publication Data
US 2005/0137394 A1    Jun. 23, 2005

(30) Foreign Application Priority Data
Oct. 9, 2003   (KR)   .................... 10-2003-0070184

(51) Int. Cl.
*C07D 487/22*   (2006.01)
(52) U.S. Cl. .................................... 540/145
(58) Field of Classification Search ............... 540/145
See application file for complete search history.

(56) References Cited
U.S. PATENT DOCUMENTS 6,048,630 A    4/2000   Burrows et al.
6,303,238 B1   10/2001  Thompson et al.
6,420,648 B1 * 7/2002   Lindsey ...................... 136/263
2001/0053463 A1  12/2001 Thompson et al.

* cited by examiner

*Primary Examiner*—Shaojia Anna Jiang
*Assistant Examiner*—Ganapathy Krishnan
(74) *Attorney, Agent, or Firm*—Birch, Stewart, Kolasch & Birch, LLP

(57) ABSTRACT

The present invention relates to emitting compounds for organic electroluminescent device, particularly to porphines-platinum metal complex compounds represented by the following formula (1):

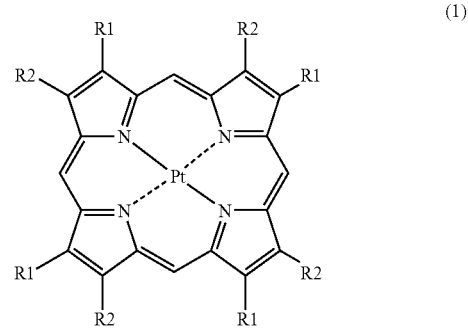

(1)

wherein $R_1$ and $R_2$ are as defined in the specification.

In addition, the present invention relates to an organic electroluminescent device comprising the above material which has high luminescence efficiency, enhanced operating life time, and high purity of red chromaticity.

2 Claims, 2 Drawing Sheets

[FIG. 1]
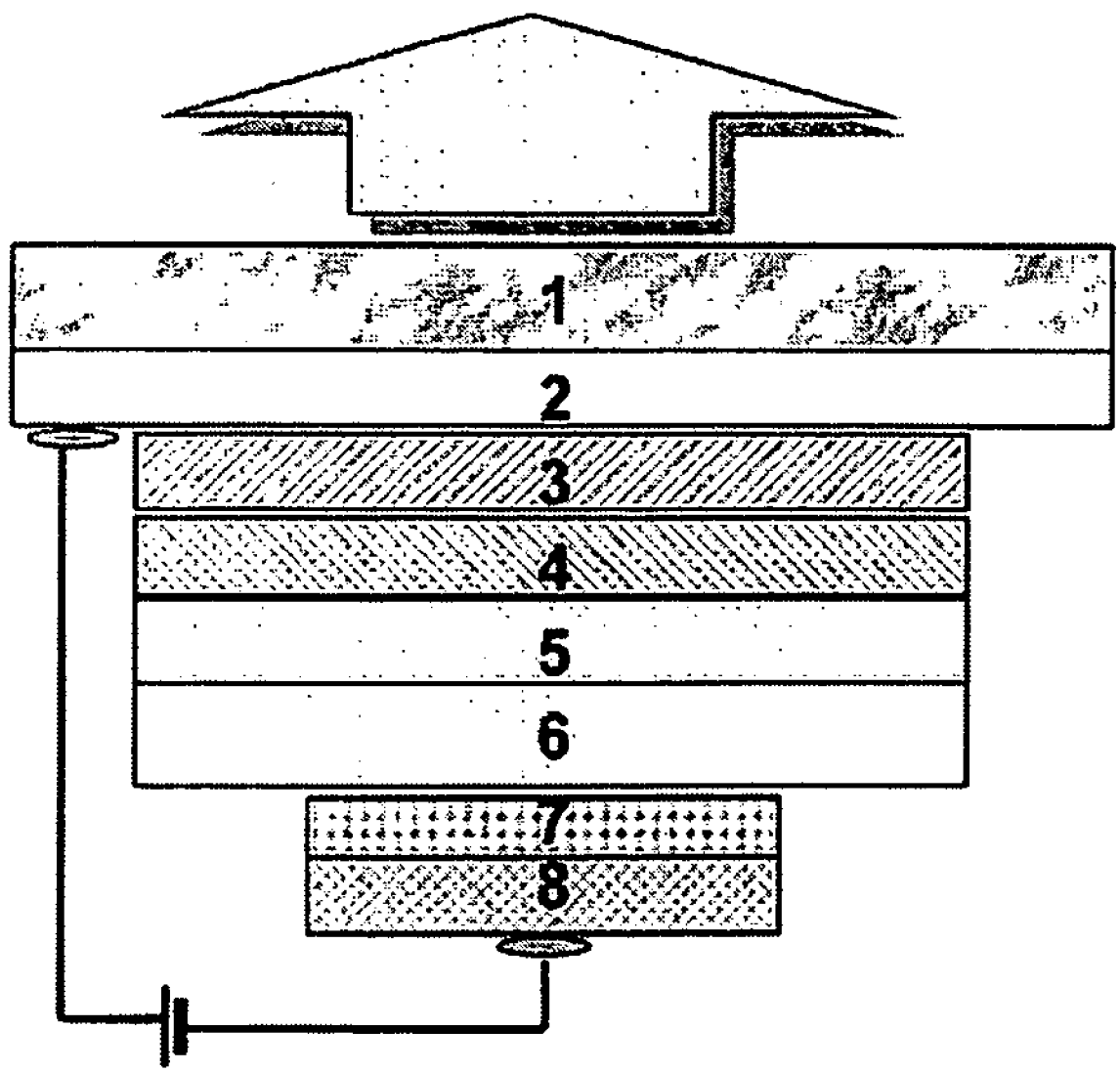

[FIG. 2]
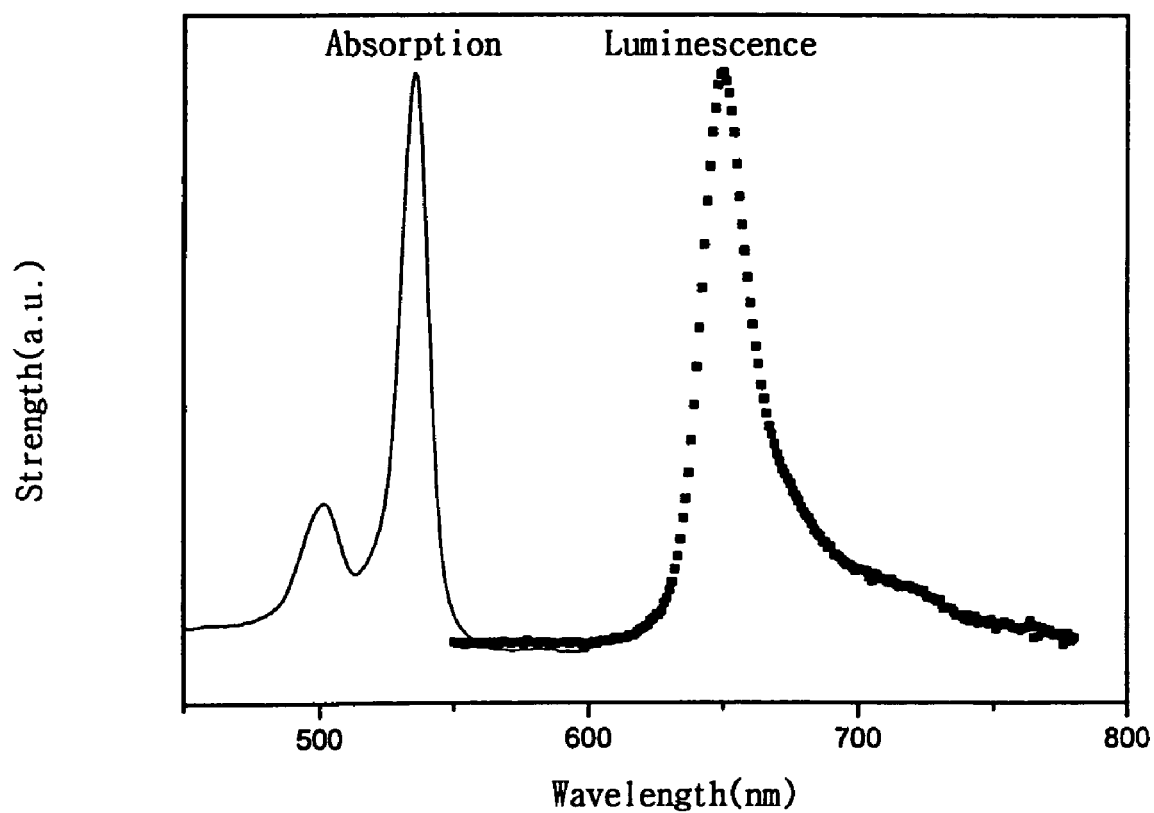

PORPHINES-PLATINUM METAL COMPLEX COMPOUNDS FOR ORGANIC ELECTROLUMINESCENT DEVICE AND ORGANIC ELECTROLUMINESCENT DEVICE USING THEM

This Nonprovisional application claims priority under 35 U.S.C. § 119(a) on Patent Application No(s). 10-2003-0070184 filed in Korea, Republic of on Oct. 9, 2003, the entire contents of which are hereby incorporated by reference.

FIELD OF THE INVENTION

The present invention relates to emitting compounds for organic electroluminescent device, particularly to porphines-platinum metal complex compounds represented by the following formula (1):

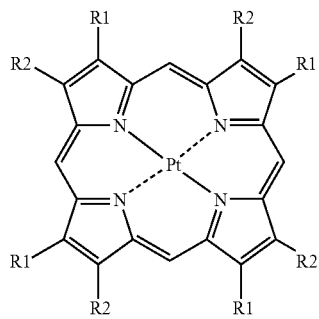

(1)

wherein $R_1$ and $R_2$ are as defined below.

In addition, the present invention relates to an organic EL device containing the porphines-platinum metal complex compounds represented by the above formula (1), particularly to an organic EL device having one or more organic thin layers comprising luminescence region formed between a first electrode and a second electrode, wherein at least any one layer of the organic thin layers comprises one or more compounds represented by the above formula (1).

BACKGROUND OF THE INVENTION

The field of display device is very important for the information and communication industry. Recently, in accordance with a speed-up in the development of information and communication technology, more highly-advanced efficiency has been asked for in this field. Display can be divided into luminescent type and non-luminescent type. The luminescent type of display comprises Cathode Ray Tube (CRT), Electroluminescence Display (ELD), Light Emitting Diode (LED), Plasma Display Panel (PDP), etc. The non-luminescent type of display comprises Liquid Crystal Display (LCD), etc.

These luminescent and non-luminescent types of displays have such basic properties as operation voltage, consumption power, brightness, contrast, response rate, life time, etc. However, LCD, which has been widely used up to now, has some problems in response rate, contrast, and sight dependency among the above basic properties. On the contrary, LED-using display can solve the above LCD problems, and also has many other advantages such as fast response speed, no need of back light due to self-emission, and excellent brightness. Thus, it is anticipated that LED-using display becomes the next-generation display device.

However, LED is mainly used with a crystal form of inorganic material, and so is hard to be applied to a large size of electroluminescent device. In addition, the electroluminescent device using inorganic material is very expensive and needs more than 200 V of operation voltage. However, Eastman Kodak reported in 1987 that the company manufactured a device made of a material having π-conjugate structure such as alumina quinine. The study for electroluminescent device using organic material has been more active thereafter.

The electroluminescence device (EL device, below) can be divided into inorganic EL device and organic EL device, depending on what material is used to form the emission layer (emitter layer).

The organic EL device, a self-emitting type of device that electrically excites fluorescent organic compound, is superior to the inorganic EL device in brightness, operation voltage, and response rate, and also can emit multi-colors.

In addition, the organic EL device is a luminescent device to emit in low voltage current, and has superior properties such as enhanced brightness, high speed of response, wide view angle, plane luminescence, slim type, and multi-color luminescence.

Thus, the organic EL device is expected to be applicable to a full-color flat panel display due to such superior properties that cannot be found in other displays.

C. W. Tang et al. reported the first practical device performance of the organic EL device in Applied Physics Letters, vol. 51 (12) pp 913-915 (1987). They developed a structure laminated with a thin film (a hole transport layer) obtained from diamine analogues and a thin film (an electron transport layer) obtained from tris(8-quinolinolate)aluminum (Alq3, below) as organic layer. The laminated structure can lower the injection barrier of electron and hole from both electrodes to the organic layer, and also can enhance the re-combination probability of electron and hole from the inner organic layer.

Later, C. Adachi et al. developed an organic EL device having an organic luminescent layer with three-laminated structure of hole transport layer, emission layer, and electron transport layer [Japanese Journal of Applied Physics, vol. 27 (2), pp L269-L271 (1988)], and two-laminated structure of hole transportable emission layer and electron transport layer [Applied Physics Letter, vol. 55 (15), pp 1489-1491 (1989)], and showed that the optimization of device property can be achieved by constructing a multi-layer structure suitable for materials and combination thereof.

The general organic EL comprises a first electrode (anode), a second electrode (cathode), and organic luminescent media. The organic luminescent media have at least two separate organic luminescent layers, i.e. one layer to inject and transport electron, and the other layer to inject and transport hole into the device. In addition, another multi-layer of thin organic film may be included. The above layers to inject and transport electron and hole each can be divided into an electron injection layer, an electron transport layer, a hole injection layer, and a hole transport layer. In addition, the organic luminescent media may be constructed with further including an emission layer besides the above layers.

The simple structure of organic EL device comprises a first electrode/an electron transport layer, and an emission layer/a second electrode. Also, the structure of organic EL device can be separated into a first electrode/a hole injection layer/a hole transport layer/an emission layer/an electron transport layer/an electron injection layer/a second electrode.

The operation principle of the organic EL device having the above structure is as follows.

If voltage is applied to the above anode and cathode, the hole injected from the anode is transferred to the emission layer via the hole transport layer. Meanwhile, the electron is injected from the cathode to the emission layer via the electron transport layer. The hole and electron are recombined in the emission layer to form exiton. The exiton is changed from the excitation state to the basic state, by which the fluorescent molecule of the emission layer becomes luminescent to form images.

At present, the material conventionally used for the hole transport layer is triphenylamine analogues. In addition, organic metal complex compounds or heterocyclic compounds are used for the electron transport layer. Organic compounds or organic metal complex compounds are solely used for the emission layer or as host of the emission layer. When organic compounds or organic metal complex compounds are used as host of the emission layer, organic luminescent materials or a metal complex type of organic luminescent materials are used as dopant, thereby controlling the color of luminescence.

The maximum quantum efficiency of luminescent materials used in an organic EL device is about 5% by theoretical calculation. If such low quantum efficiency can be enhanced, the life time of the device may be increased. Generally, fluorescence is light emitted when the molecule is fallen from the monoplet excitation state to the basic state. On the other hand, phosphorescence is light emitted when the molecule is fallen from the triplet excitation state to the basic state. In case of fluorescence, the maximum efficiency emitted from the basic state of molecule is about 25%, and in case of phosphorescence, about 75%. That is, phosphorescence has high luminescence efficiency than fluorescence, by which it is possible to extend the life of the device. Particularly, to put the full-color display into practice, it has been urgently needed to develop a material having high purity red luminescence. A present study concerns platinum metal complex organic compounds which are phosphorescence materials, as red luminescence materials having high purity and efficiency for the organic EL device (U.S. Pat. No. 6,310,360).

Metal complex organic compounds to constitute the emission layer have a different luminescent color in accordance with the molecular structure of ligand. In this case, the emission layer comprises only platinum metal complex organic compounds of phosphorescence materials, or includes platinum metal complex organic compounds of phosphorescence materials as dopant. However, phosphorescence materials having practical luminescence efficiency have not been developed yet.

In view of the above, the present inventors have conducted extensive studies to develop novel phenyl pyridine-iridium metal complex compounds of formula (1) having practical luminescence efficiency, and completed the present invention.

SUMMARY OF THE INVENTION

An object of the present invention is to provide novel porphines-platinum metal complex compounds for organic EL device represented by the formula (1).

Another object of the present invention is to provide an organic EL device having one or more organic thin layers comprising luminescence region formed between a first electrode and a second electrode, wherein at least any one layer of the organic thin layers comprises one or more compounds represented by the formula (1).

In order to accomplish these objects of the present invention, the present invention provides substituted porphines-platinum metal complex compounds, luminescence materials for organic EL device represented by the following formula (1):

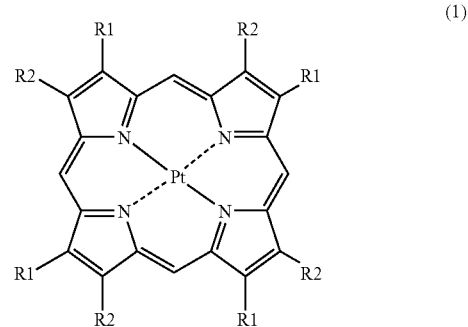

wherein $R^1$ is a straight or branched alkyl group having 1 to 10 carbon atoms, a alkoxy group having 1 to 10 carbon atoms, or a halogen group, and $R^2$ is a substituted or un-substituted aromatic group having 5 to 18 carbon atoms, a cycloalkyl group having 5 to 18 carbon atoms, and an aromatic heterocyclic group having 5 to 18 carbon atoms and one or more hetero-atoms selected from the group consisting of N, O and S.

PREFERRED EMBODIMENTS OF THE INVENTION

The definitions in the above formula will be shown in detail below.

According to the present invention, a preferable example of "alkyl group" is a straight or branched chain saturated hydrocarbon group having 1 to 10 carbon atoms, for example, methyl, ethyl, propyl, isopropyl, butyl, isobutyl, t-butyl, pentyl, isopentyl, hexyl, heptyl, octyl, nonyl, decyl, etc., but more preferably, methyl, ethyl, propyl, isopropyl, butyl, isobutyl, t-butyl, or pentyl can be used.

A preferable example of the "alkoxy group" is a group containing a straight or branched alkyl having 1 to 10 carbon atoms, for example, methoxy, ethoxy, propoxy, isopropoxy, butoxy, isobutoxy, t-butoxy, pentoxy, isopentoxy, heptoxy, etc., but more preferably, the methoxy or ethoxy group can be used.

The "halogen group" is a generic name of fluoro, chloro, bromo, and iodo.

A preferable example of the "aromatic group" is an aromatic hydrocarbon group having 5 to 18 carbon atoms, for example, phenyl, naphthyl, etc.

A preferable example of the "cycloalkyl group" is a cyclic hydrocarbon group having 5 to 18 carbon atoms, for example, cyclopentyl, cyclopentenyl cyclohexyl, cyclohexenyl cycloheptyl, cyclooctyl, etc., but more preferably, cyclohexyl group can be used.

A preferable example of the "aromatic heterocyclic group" is a mono- and polyheteroaromatic group having 5 to 18 carbon atoms, for example, pyridinyl, pyrazinyl, pyimidinyl, pyridazinyl, etc.

Also, preferable examples of the "substituents" are hydrogen atom, halogen group, cyano group, amino group, nitro group, carboxy group, methyl group, ethyl group, propyl group, butyl group, sec-butyl group, tert-butyl group, pentyl group, hexyl group, etc., but are not limited thereto.

For a first group of compounds consisted of those compounds of formula (1), $R^1$ and $R^2$ could be:

$R^1$ is a straight or branched alkyl group having 1 to 5 carbon atoms, and $R^2$ is a cycloalkyl group having 5 to 18 carbon atoms.

For a second group of compounds consisted of those compounds of formula (1), $R^1$ and $R^2$ could be:

$R^1$ is a straight alkyl group having 1 to 5 carbon atoms, and $R^2$ is a cyclohexyl.

The representative examples of formula (1) are described below.

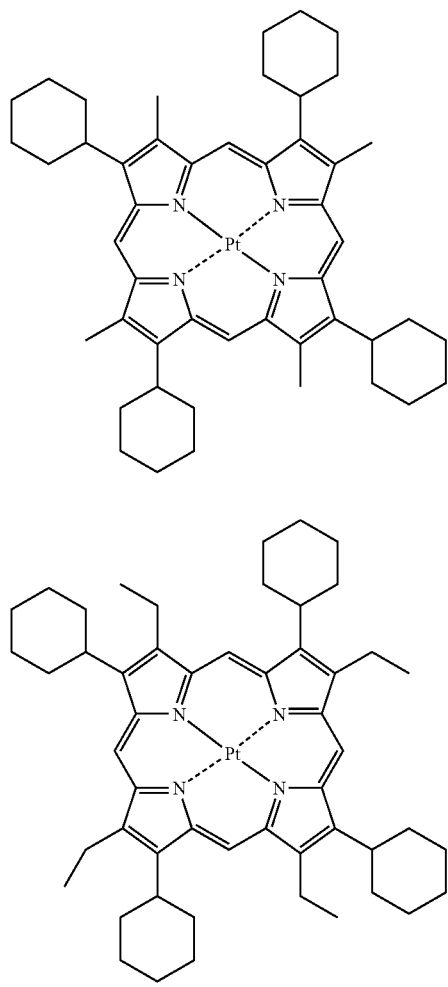

Pt-R1

Pt-R2

However, the present invention shall not be limited by these representative examples.

In addition, the present invention provides an organic EL device comprising the compound of formula (1). Specifically, the organic EL device may have one or more organic thin layers formed between a first electrode and a second electrode, wherein at least any one layer of the organic thin layers comprises one or more red color emitting materials according to the present invention.

The compound of formula (1) can be used alone, in a type of combination, or as host doped by other materials, to any of the organic thin layers, or used as dopant to the other hole transport material, emission material, or electron transport material. Preferably, the compound of the present invention can be used as dopant or host to the emission layer.

A variety of embodiments of the organic EL device using the luminescence materials of the present invention can be achieved. Basically, the emission layer, if necessary, is introduced into the pair of electrodes (anode and cathode). Then, if necessary, a hole injection layer and/or a hole transport layer and/or an electron injection layer and/or an electron transport layer can be introduced. Specifically, the structure examples of the device are: (1) anode/emission layer/cathode; (2) anode/hole transport layer/emission layer/cathode; (3) anode/hole transport layer/electron transport layer/cathode; (4) anode/hole injection layer/hole transport layer/emission layer/cathode; (5) anode/hole injection layer/hole transport layer/emission layer/electron transport layer/cathode; (6) anode/hole injection layer/hole transport layer/emission layer/electron transport layer/electron injection layer/cathode; and (7) anode/hole injection layer/emission layer/electron injection layer/cathode; and (8) anode/hole transport layer/emission layer/hole blocking layer/electron transport layer/electron injection layer/cathode, etc. If necessary, the device having the above structures is supported by substrate. No particular limitation exists for the substrate, and conventional substrates usable in the organic EL device are glass, transparent plastics, quartz, etc.

Each layer constructing the organic EL device of the present invention may be formed by applying these comprising materials under such conventional methods as deposition method, spin-coat method, or cast method, to laminate the layers.

No particular limitation exists on the thickness of each layer, such as emission layer, formed by these methods, and suitable selection may be made depending on the device conditions.

BRIEF DESCRIPTION OF THE DRAWINGS

The present invention will be more clearly understood from the detailed description in conjunction with the following drawings.

FIG. 1 is a schematic sectional view of the conventional organic EL device.

FIG. 2 is a luminescent spectrum of the organic EL device using platinum complex compound Pt—R1 of the present invention.

DETAILED DESCRIPTON OF THE INVENTION

The porphines-platinum metal complex compounds of formula (1) of the present invention and the organic EL device applied with the compounds are explained through the synthetic examples and practicing examples below. Additional advantages, objects, and features of the present invention will be set forth in the description which follows, and will also become apparent to those who practice the present invention. The objects and other advantages of the present invention will be explained in the written description including the claims.

SYNTHETIC EXAMPLES

Synthetic Example 1

1) Synthesis of Precursor of Platinum Complex Compound Pt—R1 (1)

6.02 g of cyclohexane carboxyaldehyde (50 mmole), 3.75 g of nitroethane (50 mmole), and 1.3 g of 1,8-diazabicyclo-(5,4,0)-undec-7-ene (DBU, 50 mmole) were added into 100 ml of reaction bowl, and 50 ml of purified solvent, acetonitrile, was added thereto under the flow of nitrogen, and then the reaction was performed at room temperature for 24 hours. After completing the reaction, the reaction mixture was extracted by 1 mole of hydrochloride and ethyl acetate, and then, concentrated in vacuum, and separated by silica gel column chromatography (Ethyl acetate:Hexane=1:30), to obtain 5.4 g of precursor (1) (yield: 50%).

The molecular structure of obtained material was analyzed by NMR. As a result, it was confirmed that precursor (1) was synthesized.

$^1$H NMR (CDCl$_3$): δ0.96 (t, 3H, J=7.5), 1.04-2.16 (m, 11H), 2.18-2.26 (m, 2H), 3.58-3.64 (t, 0.5H, J=5,6, C$\underline{H}$OH), 3.75-3.78 (t, 0.5H, J=3, C$\underline{H}$OH), 4.5-4.6 (m, 1H, C$\underline{H}$NO$_2$)

2) Synthesis of Precursor of Platinum Complex Compound Pt—R1 (2)

5.4 g of precursor (1) prepared by above step 1) (26 mmole), 3.4 g of copper chloride (34 mmole), and 7.7 g of 1,8-dicyclohexyl-carbodiimide (DCC, 37 mmole) were added into 100 ml of reaction bowl, and 60 ml of purified solvent, dioxane, was added thereto under the flow of nitrogen, and then the reaction was performed for 48 hours. After adding hexane solvent and filtering the mixture, the precipitate was extracted by 1 mole of hydrochloride and ethyl acetate, and then, concentrated in vacuum, and separated by silica gel column chromatography (Ethyl acetate:Hexane=1:30), to obtain 3.74 g of precursor (2) (yield: 76%).

The molecular structure of obtained material was analyzed by NMR. As a result, it was confirmed that precursor (2) was synthesized.

$^1$H NMR (CDCl$_3$): δ1.07 (t, 3H, J=7), 1.13-1.173 (m, 10H), 2.45-2.49 (m, 1H), 2.52-2.65 (q, 2H, J=8.2), 5.41 (d, 1H, J=10.4, Z—C$\underline{H}$=CHNO$_2$), 6.86-6.91 (d, 1H, J=10.4, E-C$\underline{H}$=CHNO$_2$)

3) Synthesis of Precursor of Platinum Complex Compound Pt—R1 (3)

3.74 g of precursor (2) prepared by above step 2) (20 mmole), 3.4 g of ethyl isocyanoacetate (20 mmole), and 7.7 g of DBU (30 mmole) were added into 50 ml of reaction bowl, and 30 ml of purified solvent, tetrahydrofurane, was added thereto under the flow of nitrogen, and then the reaction was performed at room temperature for 15 hours. After completing the reaction, the reaction mixture was extracted by 1 mole of hydrochloride and ethyl acetate, and then, concentrated in vacuum, and separated by silica gel column chromatography (Ethyl acetate:Hexane=1:30), to obtain 1.2 g of precursor (3) (yield: 25%).

The molecular structure of obtained material was analyzed by NMR and M/A. As a result, it was confirmed that precursor (3) was synthesized.

$^1$H NMR (CDCl$_3$): δ1.14-1.28 (t, 3H, J=14.8), 1.28-1.85 (m, 13H), 2.48-2.56 (q, 2H, J=5), 3.02-3.22 (m, 1H), 4.24-4.31(q, 2H, J=6.33), 6.63-6.65 (d, 1H, J=3)

4) Synthesis of Precursor of Platinum Complex Compound Pt—R1 (4)

1.2 g of precursor (3) prepared by above step 3) (5 mmole) and 0.4 g of LiAlH$_4$ (5.3 mmole) were added into 50 ml of reaction bowl, and 30 ml of purified solvent, tetrahydrofurane, was added thereto under the flow of nitrogen, and then the reaction was performed at 0° C. for 2 hours. 4 ml of ethyl acetate and 10 ml of 1 mole hydrochloride were added thereto, and then reaction mixture was extracted by dichloromethane and purified water. Then, 0.3 g of p-TsOH was added to the organic layer, and the reaction mixture was further reacted at room temperature for 12 hours. Subsequently, 1.4 g of tetrachlorobenzoquinone (Choranil, 5.5 mmole) was added thereto, and the reaction mixture was further reacted at room temperature for 8.5 hours, and then extracted by 5% NaHCO$_3$ and chloroform, and then, concentrated in vacuum, and separated by silica gel column chromatography (Ethyl acetate:Hexane=1:3), to obtain 190 mg of precursor (4) (yield: 20%).

The molecular structure of obtained material was analyzed by NMR. As a result, it was confirmed that precursor (4) was synthesized.

$^1$H NMR (CDCl$_3$): δ0.373 (s, 2H, NH), 1.83-2.9 (m, 13H), 4.23-4.27 (q, 2H, J=3, C$\underline{H}_2$CH$_3$), 4.29-4.34 (t, 1H, J=3.1), 10.37 (s, 4H)

5) Synthesis of Platinum Complex Compound Pt—R1

0.3 g of precursor (4) prepared by above step 4) (0.3 mmole) and Pt(II)Cl$_2$ (0.3 mmole) were added into 50 ml of reaction bowl, and 30 ml of purified solvent, benzonitrile, was added thereto under the flow of nitrogen, and then the reaction mixture was refluxed at 180° C. for 18 hours. After completing the reaction, the solvent was removed in vacuum, and separated by silica gel column chromatography (Ethyl acetate:Hexane=1:30), to obtain 100 mg of the final product, Pt—R1 (yield: 50%).

$^1$H NMR (CDCl$_3$): δ1.8-2.76 (m, 13H), 4.1-4.14 (q, 2H, J=1.6, C$\underline{H}_2$CH$_3$), 4.19-4.24 (t, 1H, J=1.6), 10.24 (s, 4H)

The above preparation step of Pt—R1 is summarized below:

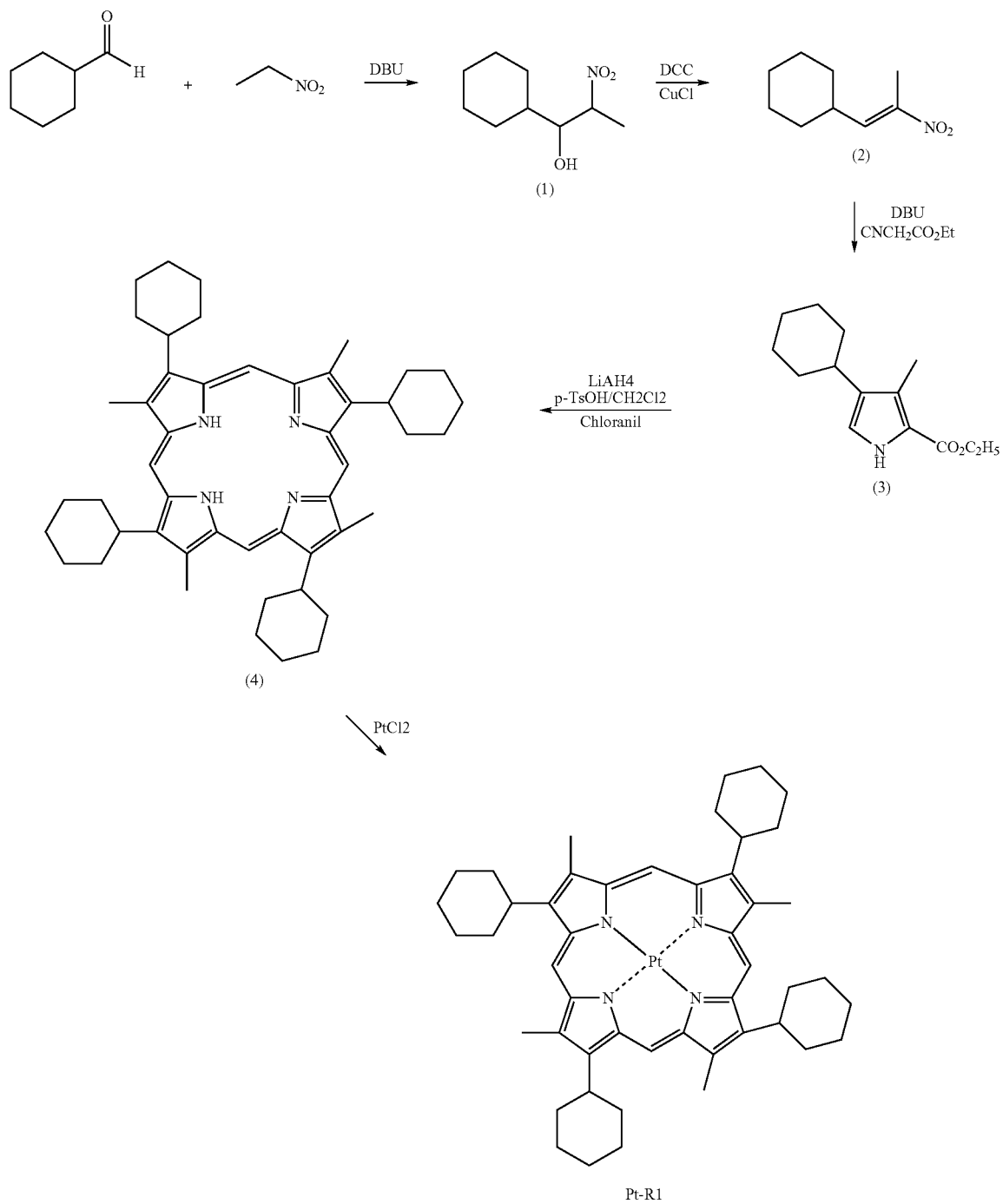

Synthetic Example 2

1) Synthesis of Precursor of Platinum Complex Compound Pt—R2 (1)

6.02 g of cyclohexane carboxyaldehyde (50 mmole), 4.25 g of nitropropane (50 mmole), and 1.3 g of DBU (50 mmole) were added into 100 ml of reaction bowl, and 50 ml of purified solvent, acetonitrile, was added thereto under the flow of nitrogen, and then the reaction was performed at room temperature for 24 hours. After completing the reaction, the reaction mixture was extracted by 1 mole of hydrochloride and ethyl acetate, and then, concentrated in vacuum, and separated by silica gel column chromatography (Ethyl acetate:Hexane=1:30), to obtain 5.2 g of precursor (1) (yield: 54%).

The molecular structure of obtained material was analyzed by NMR. As a result, it was confirmed that precursor (1) was synthesized.

¹H NMR (CDCl₃): δ0.83-2.15 (m, 14H), 3.6-3.65 (dd, 1H), 4.56-4.76 (m, 1H)

2) Synthesis of Precursor of Platinum Complex Compound Pt—R2 (2)

5.4 g of precursor (1) prepared by above step 1) (26 mmole), 3.4 g of copper chloride (34 mmole), and 7.7 g of DCC (37 mmole) were added into 100 ml of reaction bowl, and 60 ml of purified solvent, dioxane, was added thereto under the flow of nitrogen, and then the reaction was performed for 48 hours at room temperature. After adding hexane solvent and filtering the mixture, the precipitate was extracted by 1 mole of hydrochloride and ethyl acetate, and then, concentrated in vacuum, and separated by silica gel column chromatography (Ethyl acetate:Hexane=1:30), to obtain 3.65 g of precursor (2) (yield: 78%).

The molecular structure of obtained material was analyzed by NMR. As a result, it was confirmed that precursor (2) was synthesized.

¹H NMR (CDCl₃): δ1.04-1.78 (m, 10H), 2.15 (s, 3H), 2.69-2.84 (m, 1H), 5.55-5.60 (o, 1H, J=10, Z-C$\underline{H}$=CHNO₂), 6.91-6.96 (d, 1H, J=10, E-C$\underline{H}$=CHNO₂)

3) Synthesis of Precursor of Platinum Complex Compound Pt—R2 (3)

3.65 g of precursor (2) prepared by above step 2) (20 mmole), 3.4 g of ethyl isocyanoacetate (20 mmole), and 7.7 g of DBU (30 mmole) were added into 50 ml of reaction bowl, and 30 ml of purified solvent, tetrahydrofurane, was added thereto under the flow of nitrogen, and then the reaction was performed at room temperature for 15 hours. After completing the reaction, the reaction mixture was extracted by 1 mole of hydrochloride and ethyl acetate, and then, concentrated in vacuum, and separated by silica gel column chromatography (Ethyl acetate:Hexane=1:30), to obtain 1.2 g of precursor (3) (yield: 25%).

The molecular structure of obtained material was analyzed by NMR and Mass. As a result, it was confirmed that precursor (3) was synthesized.

¹H NMR (CDCl₃): δ1.31-1.45 (m, 6H), 1.66-1.90(m, 7H), 2.12 (s, 2H), 3.28-3.30 (m, 1H), 4.23-4.34 (q, 2H, J=7.1), 6.59-6.60 (d, 1H, J=2.6)

4) Synthesis of Precursor of Platinum Complex Compound Pt—R2 (4)

1.2 g of precursor (3) prepared by above step 3) (5 mmole) and 0.4 g of LiAlH₄ (5.3 mmole) were added into 50 ml of reaction bowl, and 30 ml of purified solvent, tetrahydrofurane, was added thereto under the flow of nitrogen, and then the reaction was performed at 0° C. for 2 hours. 4 ml of ethyl acetate, and 10 ml of 1 mole hydrochloride were added thereto, and then the reaction mixture was extracted by dichloromethane and purified water. Then, 0.3 g of p-TsOH was added to the organic layer, and the reaction mixture was further reacted at room temperature for 12 hours. Subsequently, 1.4 g of tetrachlorobenzoquinone (Choranil, 5.5 mmole) was added thereto, and the reaction mixture was further reacted at room temperature for 8.5 hours, and then extracted by 5% NaHCO₃ and chloroform, and then, concentrated in vacuum, and separated by silica gel column chromatography (Ethyl acetate:Hexane=1:3), to obtain 190 mg of precursor (4) (yield: 20%).

The molecular structure of obtained material was analyzed by NMR and M/A. As a result, it was confirmed that precursor (4) was synthesized.

¹H NMR (CDCl₃): δ3.75 (s, 2H, NH), 1.79-2.81 (m, 10H), 3.62-3.68 (t, 3H, J=5, CH₃), 4.18-4.36 (m, 1H), 10.45 (3s, 4H)

5) Synthesis of Platinum Complex Compound Pt—R2

190 mg of precursor (4) prepared by above step 4) (0.3 mmole) and Pt(II)Cl₂ (0.3 mmole) were added into 50 ml of reaction bowl, and 30 ml of purified solvent, benzonitrile, was added thereto under the flow of nitrogen, and then the reaction materials were refluxed at 180° C. for 18 hours. After completing the reaction, the solvent was removed in vacuum, separated by silica gel column chromatography (Ethyl acetate:Hexane=1:30), to obtain 100 mg of the final product, Pt—R2 (yield: 50%).

¹H NMR (CDCl₃): δ1.63-2.71 (m, 10H), 3.54-3.59 (t, 3H, J=5, CH₃), 4.12-4.26 (m, 1H), 9.93-10.36 (3s, 4H)

The above preparation step of Pt—R1 is summarized below:

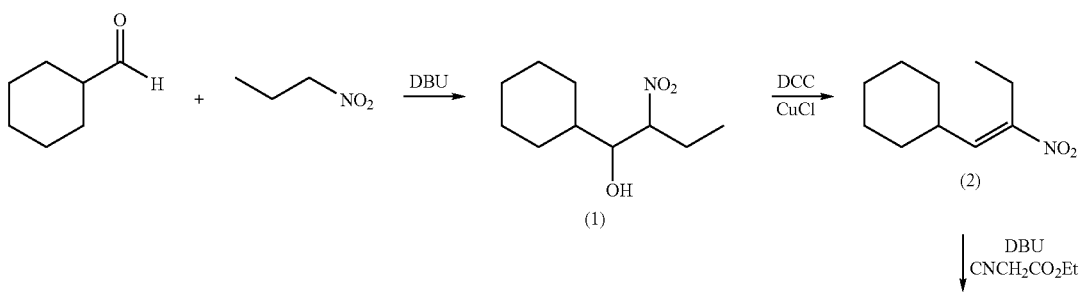

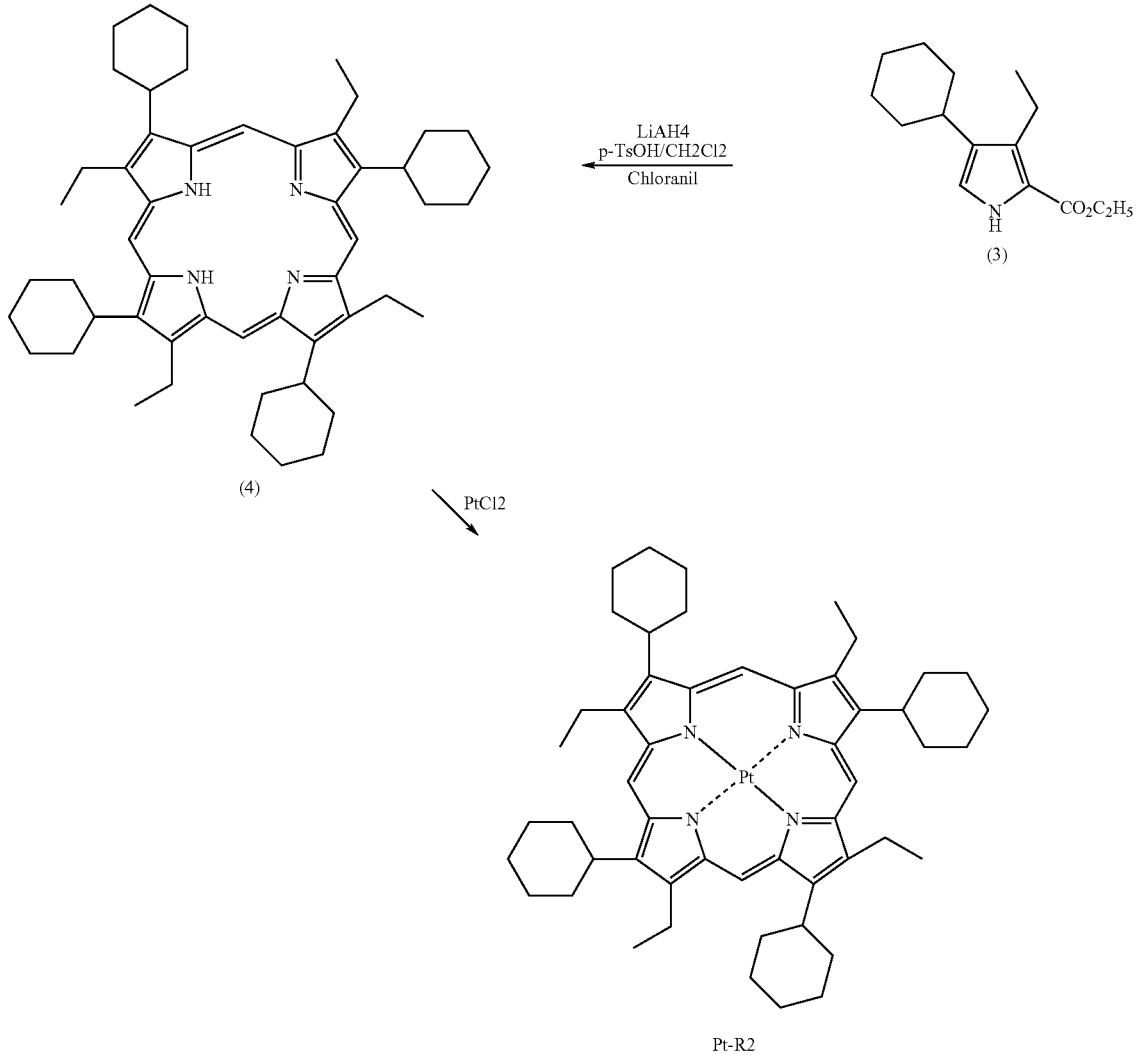

The above synthesized materials were further purified with a vacuum sublimation apparatus to use in the organic EL device.

Example 1

For the present example, the organic EL device using Pt—R1 as dopant and 4,4'-Bis(carbazole-9-yl)-biphenyl (CBP) as host of a red color emitting layer was manufactured.

First, a hole transport layer was formed with the thickness of 50 nm by depositing N,N'-dinaphthyl-N,N'-phenyl(1,1'-biphenyl)-4,4'-diamine in vacuum on an ITO-deposited glass washed by microwave. Then, an emission layer is formed with the thickness of 30 nm on the hole transport layer by depositing CBP (host), which was doped with Pt—R1 (dopant) by 10%. A hole blocking layer [2,9-dimethyl-4,7-diphenyl-1.10-phenanthroline (BCP; 5 nm)], an electron transport layer (Alq3; 40 nm), an electron injection layer ($Li_2O$; 25 nm), and a cathode (Mg/Ag; 100 nm) were deposited in vacuum in the order thereon by, to complete the organic EL device.

Direct voltage of forward bias was applied to the organic EL device manufactured by Example 1, and luminescent property thereof was evaluated. The luminescent color was red according to FIG. 2. As a result of spectroscopy, a spectrum having approximately 605 nm of luminescent peak was obtained, and the value of color coordinates was x=0.690 and y=0.30. In addition, as a result of voltage-brightness test, 172 cd/m$^2$ of brightness at 6.7 V was obtained, at which point the efficiency was 0.9 lm/W.

Example 2

For the present example, the organic EL device was manufactured under the same conditions as Example 1, except using Pt—R2 as dopant and CBP as host of a red color emitting layer, which was doped with Pt—R2 by 10%.

Direct voltage of forward bias was applied to the organic EL device manufactured by Example 2, and luminescent property thereof was evaluated. The luminescent color was red. As a result of spectroscopy, a spectrum having approximately 617 nm of luminescent peak was obtained, and the value of color coordinates was x=0.68 and y=0.30. In addition, as a result of voltage-brightness test, 196 cd/m² of brightness at 7 V was obtained, at which point the efficiency was 1.0 lm/W.

Comparative Example 1

For the present example, the organic EL device was manufactured under the same conditions as Example 1, except using 2,3,7,8,12,13,17,18-octaethyl-21H,23H-porphine platinum (III) (PtOEP) as dopant and CBP as host of a red color emitting layer, which was doped with Pt—R2 by 10%.

Direct voltage of forward bias was applied to the organic EL device manufactured by Comparative example 1, and luminescent property thereof was evaluated. The luminescent color was red. As a result of spectroscopy, a spectrum having approximately 645 nm of luminescent peak was obtained, and the value of color coordinates was x=0.68 and y=0.30. In addition, as a result of voltage-brightness test, 149 cd/m² of brightness at 6.9 V was obtained, at which point the efficiency was 0.8 lm/W.

As shown in the above results, the organic EL devices applied with the novel red color emitting materials of the present invention show more highly advanced luminescent efficiency and high value of color coordinates than the organic EL device applied with conventional red color emitting materials. Accordingly, the organic EL device according to the present invention can achieve practical luminescence efficiency and enhanced operating life time and stability.

It will be apparent to those skilled in the art that various modifications and variations can be made for the present invention. Therefore, it is intended that the present invention covers those modifications and variations of this invention that come within the scope of the appended claims, and their equivalents.

INDUSTRIAL APPLICABILITY

The organic EL devices applied with novel porphines-platinum metal complex compounds according to the present invention can achieve practical luminescence efficiency, enhanced operating life time, and high purity of red chromaticity.

What is claimed is:

1. A compound represented by the following formula (1):

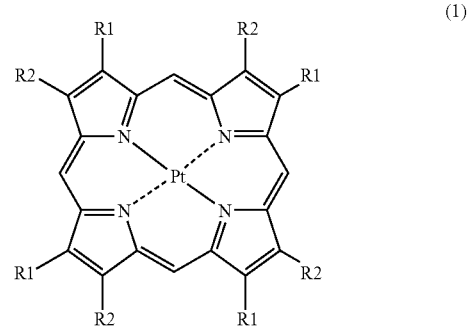

wherein $R^1$ is a straight or branched alkyl group having 1 to 10 carbon atoms, an alkoxy group having 1 to 10 carbon atoms, or a halogen group, and
$R^2$ is a substituted or un-substituted aromatic heterocyclic group having 5 to 18 carbon atoms and one or more hetero-atoms selected from the group consisting of O and S.

2. The compound according to claim 1, wherein $R^1$ is a straight or branched alkyl group having 1 to 10 carbon atoms.

* * * * *